United States Patent
Razouane et al.

(10) Patent No.: US 10,013,542 B2
(45) Date of Patent: Jul. 3, 2018

(54) BIOMETRIC INTERFACE SYSTEM AND METHOD

(71) Applicant: BRAGI GmbH, München (DE)

(72) Inventors: Mohamed Ali Razouane, München (DE); Peter Vincent Boesen, München (DE)

(73) Assignee: BRAGI GmbH, München (DE)

( * ) Notice: Subject to any disclaimer, the term of this patent is extended or adjusted under 35 U.S.C. 154(b) by 0 days.

(21) Appl. No.: 15/497,065

(22) Filed: Apr. 25, 2017

(65) Prior Publication Data

US 2017/0316192 A1    Nov. 2, 2017

Related U.S. Application Data

(60) Provisional application No. 62/328,915, filed on Apr. 28, 2016.

(51) Int. Cl.
*G06F 21/32* (2013.01)
*H04R 5/04* (2006.01)
(Continued)

(52) U.S. Cl.
CPC .......... *G06F 21/32* (2013.01); *A61B 5/1172* (2013.01); *G06F 21/40* (2013.01); *G06F 21/83* (2013.01);
(Continued)

(58) Field of Classification Search
CPC .......... G06F 21/32; G06F 21/40; G06F 21/83; G06F 17/30294; G06F 17/30595;
(Continued)

(56) References Cited

U.S. PATENT DOCUMENTS

| 3,934,100 A | 1/1976 | Harada |
|---|---|---|
| 4,150,262 A | 4/1979 | Ono |

(Continued)

FOREIGN PATENT DOCUMENTS

| CN | 204244472 U | 4/2015 |
|---|---|---|
| CN | 104683519 A | 6/2015 |

(Continued)

OTHER PUBLICATIONS

Akkermans, "Acoustic Ear Recognition for Person Identification", Automatic Identification Advanced Technologies, 2005 pp. 219-223.

(Continued)

*Primary Examiner* — Mohamed Barakat
(74) *Attorney, Agent, or Firm* — Goodhue, Coleman & Owens, P.C.

(57) ABSTRACT

A system includes a wearable device having at least one sensor configured to determine a user's fingerprint data, at least one data storage device containing authentication data, and at least one processor configured to compare the user's fingerprint data with the authentication data in order to authenticate a user. A method of authenticating a wearable device includes producing a fingerprint, determining fingerprint data derived from the fingerprint with one or more sensors, comparing the fingerprint data with authentication data on one or more data storage devices, and authenticating the user if the fingerprint data and the authentication data match.

8 Claims, 2 Drawing Sheets

(51) Int. Cl.

| | | |
|---|---|---|
| *G06F 21/40* | (2013.01) | |
| *A61B 5/1172* | (2016.01) | |
| *G07C 9/00* | (2006.01) | |
| *G06F 21/83* | (2013.01) | |
| *G06F 17/30* | (2006.01) | |
| *G06F 21/34* | (2013.01) | |
| *G05B 19/00* | (2006.01) | |
| *H04Q 9/00* | (2006.01) | |

(52) U.S. Cl.
CPC ..... *G07C 9/00071* (2013.01); *G07C 9/00158* (2013.01); *H04R 5/04* (2013.01); *G05B 19/00* (2013.01); *G06F 17/30294* (2013.01); *G06F 17/30595* (2013.01); *G06F 21/34* (2013.01); *G06F 2221/2147* (2013.01); *H04Q 9/00* (2013.01)

(58) Field of Classification Search
CPC ............ G06F 21/34; G06F 2221/2147; A61B 5/1172; G07C 9/00071; G07C 9/00158; H04R 5/04; H04Q 9/00
See application file for complete search history.

(56) References Cited

U.S. PATENT DOCUMENTS

| | | |
|---|---|---|
| 4,334,315 A | 6/1982 | Ono et al. |
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,825,626 B2 | 11/2010 | Kozisek |
| 7,979,035 B2 | 7/2011 | Griffin et al. |
| 7,983,628 B2 | 7/2011 | Boesen |
| 8,095,188 B2 | 1/2012 | Shi |
| 8,140,357 B1 | 3/2012 | Boesen |
| 8,300,864 B2 | 10/2012 | Müllenborn et al. |
| 8,436,780 B2 | 5/2013 | Schantz et al. |
| 8,719,877 B2 | 5/2014 | VonDoenhoff et al. |
| 8,891,800 B1 | 11/2014 | Shaffer |
| 8,994,498 B2 | 3/2015 | Agrafioti et al. |
| 9,013,145 B2 | 4/2015 | Castillo et al. |
| 9,037,125 B1 | 5/2015 | Kadous |
| 9,081,944 B2 | 7/2015 | Camacho et al. |
| 9,510,159 B1 | 11/2016 | Cuddihy et al. |
| 9,684,778 B2 * | 6/2017 | Tharappel ............... G06F 21/32 |
| 2001/0005197 A1 | 6/2001 | Mishra et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0258412 A1 | 11/2006 | Liu |
| 2008/0090622 A1 | 4/2008 | Kim et al. |
| 2008/0146890 A1 | 6/2008 | LeBoeuf et al. |
| 2008/0254780 A1 | 10/2008 | Kuhl et al. |
| 2009/0017881 A1 | 1/2009 | Madrigal |
| 2009/0041313 A1 * | 2/2009 | Brown .................... H04M 1/05 382/124 |
| 2009/0073070 A1 | 3/2009 | Rofougaran |
| 2009/0240947 A1 * | 9/2009 | Goyal .................. H04L 9/3271 713/176 |
| 2009/0296968 A1 | 12/2009 | Wu et al. |
| 2010/0033313 A1 | 2/2010 | Keady et al. |

(56) References Cited

U.S. PATENT DOCUMENTS

| | | | |
|---|---|---|---|
| 2010/0075631 A1* | 3/2010 | Black | H04M 1/05 |
| | | | 455/410 |
| 2010/0203831 A1 | 8/2010 | Muth | |
| 2010/0320961 A1 | 12/2010 | Castillo et al. | |
| 2011/0286615 A1 | 11/2011 | Olodort et al. | |
| 2012/0159617 A1* | 6/2012 | Wu | G06F 21/445 |
| | | | 726/19 |
| 2013/0200999 A1* | 8/2013 | Spodak | G05B 1/01 |
| | | | 340/5.65 |
| 2014/0122116 A1 | 5/2014 | Smythe | |
| 2014/0163771 A1 | 6/2014 | Demeniuk | |
| 2014/0185828 A1 | 7/2014 | Helbling | |
| 2014/0222462 A1 | 8/2014 | Shakil et al. | |
| 2014/0270227 A1 | 9/2014 | Swanson | |
| 2014/0270271 A1 | 9/2014 | Dehe et al. | |
| 2015/0028996 A1 | 1/2015 | Agrafioti et al. | |
| 2015/0148989 A1 | 5/2015 | Cooper et al. | |
| 2015/0245127 A1 | 8/2015 | Shaffer | |
| 2016/0033280 A1 | 2/2016 | Moore et al. | |
| 2016/0073189 A1 | 3/2016 | Lindén et al. | |

FOREIGN PATENT DOCUMENTS

| | | |
|---|---|---|
| CN | 104837094 A | 8/2015 |
| EP | 1017252 A2 | 7/2000 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 15, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Californa (2017).
Last Push Before the Kickstarter Campaign Ends on Monday 4pm CET (Mar. 28, 2014).
Lovejoy: "Touch ID built into iPhone display one step closer as third-party company announces new tech", "http://9to5mac.com/2015/07/21/virtualhomebutton/" (Jul. 21, 2015).
Nigel Whitfield: "Fake tape detectors, 'from the stands' footle and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash-A Word From Our Software, Mechanical and Acoustics Team + An Update (Mar. 11, 2014).
Update From BRAGI—$3,000,000—Yipee (Mar. 22, 2014).

* cited by examiner

BIOMETRIC INTERFACE SYSTEM AND METHOD

PRIORITY STATEMENT

This application claims priority to U.S. Provisional Patent Application 62/328,915, filed on Apr. 28, 2016, and entitled Biometric Interface System and Method, hereby incorporated by reference in its entirety.

FIELD OF THE INVENTION

The present invention relates to wearable devices especially earpieces. More particularly, but not exclusively, the present invention relates to authentication of such devices.

BACKGROUND

Data authentication for wearable devices remains a challenge. The limited size of most wearable devices makes it difficult to design a sound and effective data authentication system that is also user friendly. One possible method to overcome this relates to the use of fingerprint analysis.

SUMMARY

It is a primary object, feature, or advantage to improve over the state of the art.

It is a further object, feature, or advantage to use fingerprint analysis to provide data authentication for wearable devices including earpieces.

It is a still further object, feature, or advantage to provide for fingerprint analysis and verification using a contact surface of an earpiece wearable.

It is another object, feature, or advantage to use ultrasound, infrared, or radar sensor units to determine a fingerprint analysis on the surface of the device and in performing the analysis to use data stored on the device or stored elsewhere.

It is a further object, feature, or advantage to allow for access to programming on a device or access to remote programming provided through a device to only be accessible once a verification of identity is provided.

It is a still further object, feature, or advantage to allow for coordination of fingerprint identification with other biometric identity criteria.

Another object, feature, or advantage is to allow for storage of fingerprints in an isolated segment of the device away from capturable data.

Yet another object, feature, or advantage is to allow for biometric data to be stored in the cloud for remove verification of user identity.

A further object, feature, or advantage is to allow for a split verification scheme for user identity so that neither the cloud nor the device alone verify, only the combination of the two can be used to identify a user.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an object, feature, or advantage stated herein.

According to another aspect, an earpiece is provided. The earpiece includes an earpiece housing, a processor disposed within the earpiece, and a fingerprint sensor operatively connected to the processor. The processor is configured to receive fingerprint data from the fingerprint sensor and compare the fingerprint data to stored fingerprint data and/or to provide authentication of a user of the earpiece.

According to another aspect, an earpiece wearable includes an earpiece housing, at least, one speaker, at least one microphone, a processor disposed within the earpiece housing and operatively connected to the at least one speaker and the at least one microphone, and a sensor operatively connected to the processor. The processor is configured to receive fingerprint data from the sensor at a contact surface on the earpiece housing and analyze the fingerprint data using stored fingerprint authentication data to make an authentication decision based on the fingerprint data. The earpiece may further include a data storage device disposed within the ear piece housing and operatively connected to the processor, wherein the stored fingerprint authentication data is stored within the data storage device. The earpiece may further include a radio transceiver disposed within the earpiece housing and operatively connected to the processor, wherein the stored fingerprint authentication data is stored at a remote location and accessible over a network through the radio transceiver. The earpiece may include both a data storage device disposed within the ear piece housing and operatively connected to the processor, wherein a first portion of the stored fingerprint authentication data is stored within the data storage device and a radio transceiver disposed within the earpiece housing and operatively connected to the processor, wherein a second portion of the stored fingerprint authentication data is stored at a remote location and accessible aver a network through the radio transceiver. Both the first portion of the stored fingerprint authentication data and the second portion of the stored fingerprint authentication data may be needed by the processor to make the authentication decision based on the fingerprint data. The earpiece may further include a gesture control interface operatively connected to the processor, wherein the gesture control interface is configured to receive gestures. The sensor may be an optical sensor and the optical sensor may be used by the gesture control interface to receive the gestures and to sense the fingerprint data. The sensor may be an Ultrasound sensor, radar sensor or other type of sensor. The processor may be further configured to process audio data from the at least one microphone and wherein the authentication decision is based on the fingerprint data and the audio data. The processor may also be further configured to process pulse oximetry data from a pulse oximeter disposed within the housing and operatively connected to the processor and the authentication decision may be based on the fingerprint data and the pulse oximetry data.

According to another aspect, a method is provided for authenticating of a user of an earpiece having an earpiece housing, at least one speaker, at least one microphone, a processor disposed within the earpiece housing and operatively connected to the at least one speaker and the at least one microphone, and a sensor operatively connected to the processor. The method includes acquiring fingerprint data using the sensor from a finger of a user contacting a fingerprint contact area on the earpiece housing, and analyzing the fingerprint data using stored fingerprint authentication data to make an authentication decision based on the fingerprint data. The stored fingerprint authentication data may be stored within the data storage device. The earpiece may further include a radio transceiver disposed within the earpiece housing and operatively connected to the processor, and the method may include accessing the stored fingerprint authentication data from a remote location over a network and through the radio transceiver. The method may further provide for accessing a first portion of the stored fingerprint authentication from the data storage device and accessing a second portion of the stored fingerprint authentication data from a remote location over a network and through the radio transceiver.

DETAILED DESCRIPTION

Figure 1:
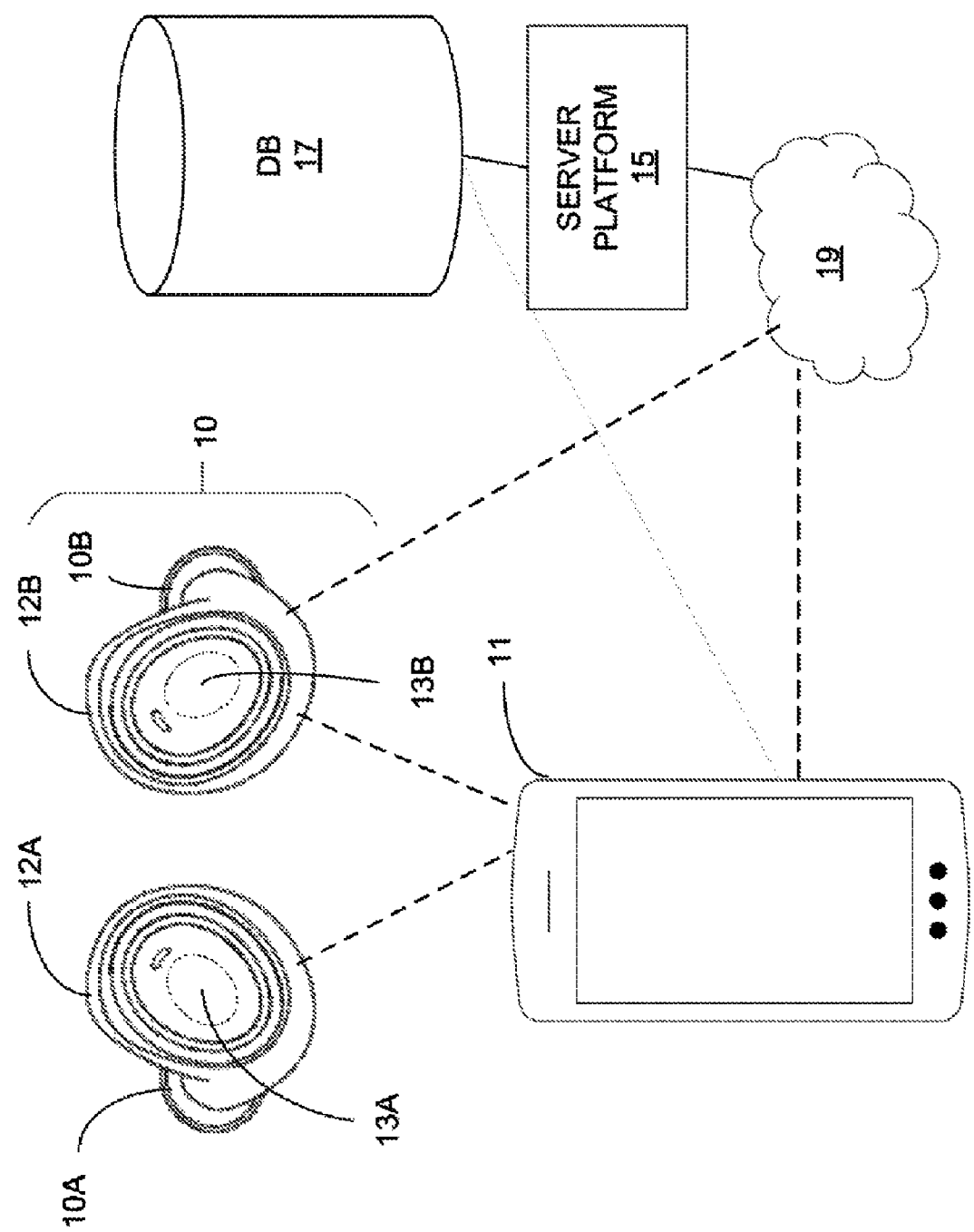
FIG. 1 illustrates one example of a system including an earpiece wearable with a fingerprint sensor used for authentication.

A wearable device and related systems and methods are shown which allow for the authentication of a user's identity using fingerprint data alone and/or in combination with additional biometric data. FIG. 1 illustrates a wearable device or system which 10 includes a first earpiece 10A with an earpiece housing 12B and a second earpiece 10B with an earpiece housing 10B. A fingerprint contact area 13A is shown for the first earpiece 10A and a fingerprint contact area 131 is shown for the second earpiece 10B. When a finger of a user is presented at one of the finger contact areas 13A, 13B, fingerprint data is acquired which may then be used to perform authentication of a user. One or more sensors are associated with each fingerprint contact area 13A, 13B. Such sensors may also be used for other purposes as well.

To perform authentication, the fingerprint data obtained from a user at the one or more finger contact areas 13A, 13B, may be compared with data stored within the first earpiece 10A or the second earpiece 10B. The data may be stored in an isolated segment of the device away from capturable data to enhance security. The data may be encrypted to enhance security. Alternatively, the fingerprint data may be compared with data stored on another device such as a mobile device 11, or data stored remotely such as in a database 17 in operative communication with a server platform 15 which may be accessible through network 19 such as the Internet. Fingerprint data or other authentication data may be stored either at the wearable device(s) 10, a mobile device 11, at a remote database 17, or at a combination of locations. For example, a portion of the authentication data may be stored at the wearable device 10A, 10B and another portion of the authentication data may be stored at the mobile device 11 or the remote database 17 in order to provide additional security. In this type of split verification scheme for user identity neither the cloud nor the device alone can provide verification, instead only a combination of the two would allow for verification or authentication of a user. Once authentication occurs all or portions of device operations or programming may become accessible to a user.

Figure 2:
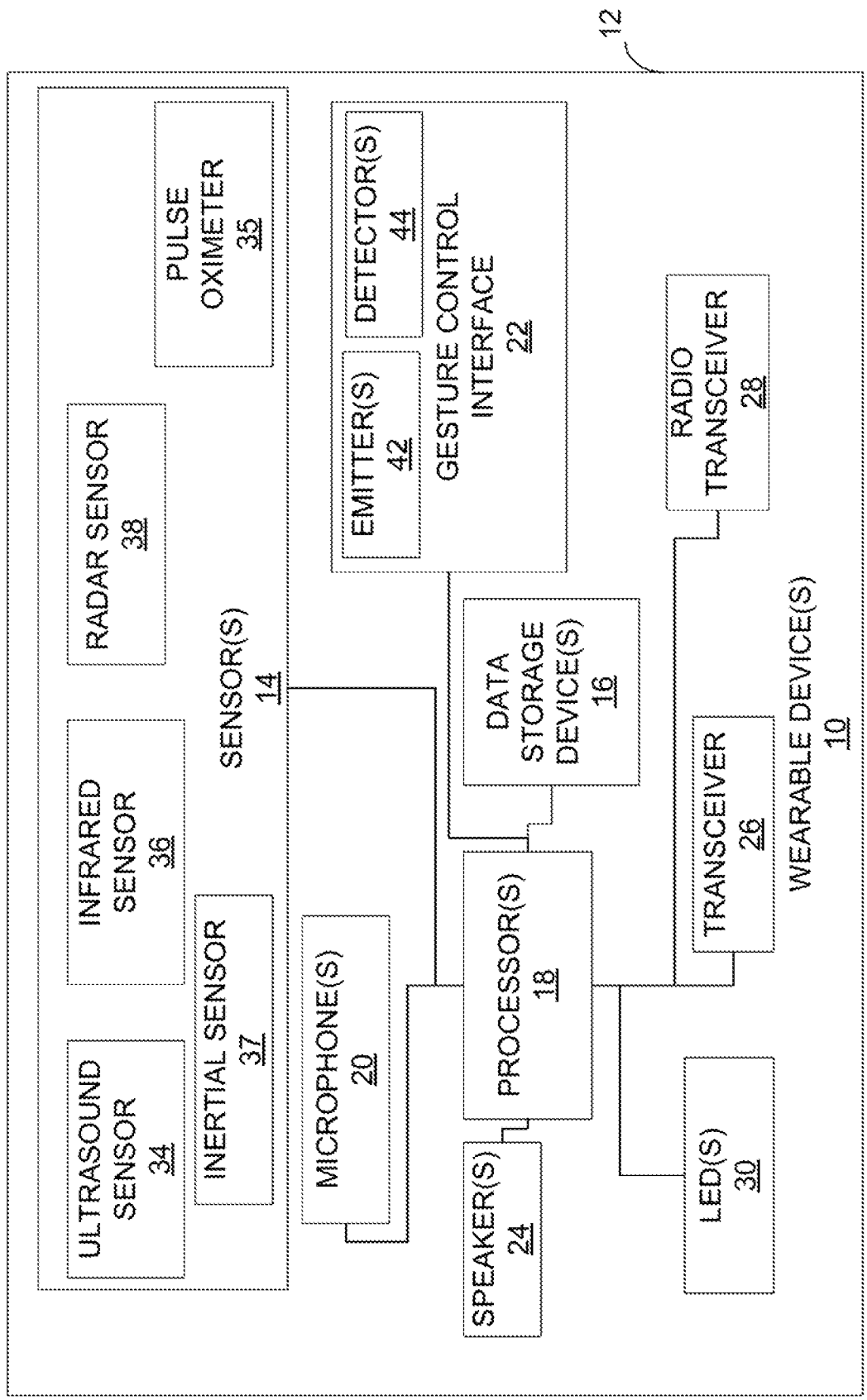
FIG. 2 is another block diagram illustrating an earpiece wearable.

FIG. 2 illustrates a wearable device such as an earpiece 10 with an ear piece housing 12. A plurality of sensors 14 are operatively connected to one or more processors 18. The sensors 14 may include an ultrasound sensor 34, an infrared sensor 36, a radar sensor unit 38, or other types of sensors. In addition, one or more microphones 20 may be present. The microphones 20 may include one or more bone microphones and/or one or more air conduction microphones. One or more speakers 24 are also present and are operatively connected to the processor(s) 18. A data storage device 16 may also be operatively connected to the processor(s) 18 and may be used for storing fingerprint data or other biometric data which is used as a part of an authentication processor. A gesture control interface 22 may also be operatively connected to the processor(s) 18. The gesture control interface 22 may include one or more emitters 42 and detectors 44. For example, the gesture control interface 22 may include optical emitters and detectors which are used to determine gestures made by a user of the earpiece. Thus, for example, the user may tap the earpiece, with a single tap or multiple taps, swipe across the ear piece, or tap and hold their finger at a surface of the earpiece. The same fingerprint contact area may be used for receiving gestures as well as for reading a fingerprint of a user. The same sensors such as optical emitters and detectors may be used to sense gestures as well as to sense fingerprints.

Instead of using the emitters 42 and detectors 44 of the gesture control interface 22, fingerprints may be detected using other types of sensors such as the ultrasound sensor 34, the infrared sensor 36, or the radar sensor 38. Each of these sensors may also be used for other purposes as well in addition to detecting fingerprints.

One or more LEDs 30 may be operatively connected to the processor(s) 18 and used for conveying information to a user or others. In addition, one or more transceivers may be present and operatively connected to the processor(s) 18. A first transceiver 26 may be a near field magnetic induction (NFMI) or other type of transceiver. One use of such a transceiver is for communication between wearable devices, such as communication between a left earpiece and a right earpiece. A radio transceiver 28 is also present and operatively connected to the processor(s) 18. The radio transceiver 28 may be a Bluetooth transceiver, Wi-Fi transceiver, or other type of radio transceiver.

Returning to the sensors 14, one or more biometric sensors may be present such as a pulse oximeter 35. The pulse oximeter 35 may be used to measure pulse of a user. It is to be further understood that characteristics of the pulse of a user may be used to further authenticate a user. For example, heart rate variability as determined using the pulse oximeter 35 or otherwise may be used to authenticate a user. An inertial sensor 37 is also shown. It is also to be understood that the inertial sensor 37 may be used to detect gait of a user or other motion of a user which may be used in authenticating a user. It is to be further understood that voice samples of a user received at one or more of the microphones 20 may be used to authenticate a user through voice analysis. Thus, in addition to fingerprint data other types of biometric data may be used to provide for further authentication of a user. Although various types of biometric sensors are shown are described, it is to be understood that other types of biometric sensors may be used.

It is to be further understood that additional or secondary authentication may be performed in a number of different ways depending upon the type of wearable device and the sensors present. For example, where voice is used as a type of secondary authentication, a determination can be made as to whether the voice of the user matches the voice of the known user. Alternatively, or in addition, the user may be asked to provide a passphrase. Similarly, where gestures are used, a user may be asked to input a series of gestures which serves as a password or passphrase to authenticate the user. Thus, it is to be understood that voice detection, heart rate variability, predetermined vocal passwords, audio playback tonal password selections, or other types of authentication may be used in addition to the fingerprint analysis. It is to be further understood that different levels of access to data or programming within the earpiece or functionality provided by the earpiece may be provided with different types of authentication. It is further to be understood that user verification at an earpiece or other wearable device may be used within a connected environment.

In operation, a fingerprint is sensed with one or more sensors. For example, a user may press their finger against a fingerprint contact area of an earpiece. Sensors such as optical sensors may be used to acquire fingerprint data such as data sufficient to define an image of a fingerprint or to describe fingerprint features. Once acquired, this data may be compared to other data identifying one or more authorized users of the earpiece. Such data may be present within the earpiece such as in a segregated portion of a memory that is not generally otherwise accessible. If the fingerprint data is a match to an authorized user then the user may be authenticated and provided access to the earpiece, be allowed to modify operational states of the earpiece such as to access a particular program or perform particular functions. If not, then the user will not be able to use the earpiece, have limited access to the earpiece, or be required to otherwise authenticate themselves. The fingerprint authentication may serve as an initial authentication and additional authentication may be required. In addition, a user may be required to re-authenticate when performing various functions if additional security requirements are associated with those functions. Where the gesture interface is used in providing for the fingerprint sensing, at times when the gesture interface is used to provide a gesture, fingerprint data may be collected at that time to re-authenticate a user via fingerprint in the background without requiring any additional activity from the user unless the authentication process fails.

Therefore, various methods, systems, and apparatus have been shown and described. Although various embodiments have been shown the present invention contemplates numerous options, variations, and alternatives including variations in the type of wearable device, whether authentication occurs on board the wearable device or at a remote location, the type of authentication data included such as fingerprint, voiceprint, gesture or gesture sequence, or other type of authentication data, plus other options, variations, and alternatives.

What is claimed is:

1. An earpiece for authenticating users using stored fingerprint authentication data, the earpiece comprising:
    an earpiece housing;
    at least one speaker;
    at least one microphone;
    a processor disposed within the earpiece housing and operatively connected to the at least one speaker and the at least one microphone;
    a sensor operatively connected to the processor;
    a data storage device disposed within the earpiece housing and operatively connected to the processor, wherein a first portion of the stored fingerprint authentication data is stored on the data storage device; and
    a radio transceiver disposed within the earpiece housing and operatively connected to the processor, wherein a second portion of the stored fingerprint authentication data is stored at a remote location and accessible over a network through the radio transceiver;
    wherein the processor is configured to receive fingerprint data from the sensor at a fingerprint contact surface on the earpiece housing and analyze the fingerprint data using the first portion of the stored fingerprint authentication data and the second portion of the stored fingerprint authentication data to make an authentication decision based on the fingerprint data.

2. The earpiece of claim 1 further comprising a gesture control interface operatively connected to the processor, wherein the gesture control interface is configured to receive gestures.

3. The earpiece of claim 2 wherein the sensor is an optical sensor and wherein the optical sensor is used by the gesture control interface to receive the gestures and to sense the fingerprint data.

4. The earpiece of claim 1 wherein the sensor is an ultrasound sensor.

5. The earpiece of claim 1 wherein the processor is further configured to process audio data from the at least one microphone and wherein the authentication decision is based on the fingerprint data and the audio data.

6. The earpiece of claim 1 wherein the processor is further configured to process pulse oximetry data from a pulse oximeter disposed within the earpiece housing and operatively connected to the processor and wherein the authentication decision is based on the fingerprint data and the pulse oximetry data.

7. A method for authenticating a user of an earpiece comprising an earpiece housing, a processor disposed within the earpiece housing, a sensor operatively connected to the processor, at least one speaker operatively connected to the processor, at least one microphone operatively connected to the processor, a data storage device disposed within the earpiece housing and operatively connected to the processor, and a radio transceiver disposed within the earpiece housing and operatively connected to the processor, the method comprising:
    acquiring fingerprint data using the sensor from a finger of the user contacting a fingerprint contact area on the earpiece housing;
    accessing a first portion of stored fingerprint authentication data, the first portion of the stored fingerprint authentication data stored on the data storage device;
    accessing a second portion of the stored fingerprint authentication data from a remote location over a network and through the radio transceiver; and
    analyzing the fingerprint data using the first portion of the stored fingerprint authentication data and the second portion of the stored fingerprint authentication data to make an authentication decision based on the fingerprint data.

8. An earpiece for authenticating users using stored fingerprint authentication data, the earpiece comprising:
    an earpiece housing;
    at least one speaker;
    at least one microphone;
    a processor disposed within the earpiece housing and operatively connected to the at least one speaker and the at least one microphone;
    an optical sensor operatively connected to the processor;
    a data storage device disposed within the earpiece housing and operatively connected to the processor, wherein a first portion of the stored fingerprint authentication data is stored on the data storage device; and
    a radio transceiver disposed within the earpiece housing and operatively connected to the processor, wherein a second portion of the stored fingerprint authentication data is stored at a remote location and accessible over a network through the radio transceiver;
    wherein the processor is configured to receive fingerprint data from the optical sensor at a fingerprint contact surface on the earpiece housing and analyze the fingerprint data using the first portion of the stored fingerprint authentication data and the second portion of the stored fingerprint authentication data to make an authentication decision based on the fingerprint data.

* * * * *